United States Patent [19]

Ljung

[11] 4,156,571
[45] May 29, 1979

[54] LASER MIRROR SCATTER AND REFLECTIVITY MEASURING SYSTEM

[75] Inventor: Bo H. G. Ljung, Wayne, N.J.

[73] Assignee: The Singer Company, Little Falls, N.J.

[21] Appl. No.: 831,113

[22] Filed: Sep. 7, 1977

[51] Int. Cl.$^2$ .................................... G01N 21/48
[52] U.S. Cl. .................................. 356/445; 250/206; 250/234; 356/350
[58] Field of Search ............... 356/124, 209, 106 LR; 331/94.5 S

[56] References Cited

U.S. PATENT DOCUMENTS 3,431,514   3/1969   Oshman et al. ................. 331/94.5 S

OTHER PUBLICATIONS

*Applied Optics*, vol. 16, No. 1, Jan. 1977, pp. 19-20, Sanders, V., "High-Precision Reflectivity Measurement Technique for Low Loss Laser Mirrors".
Jenkins et al., *Fundamentals of Optics*, Second Edition, McGraw-Hill, N.Y., 1950, p. 23.
Pribovy: Teckhnika Eksperiments, No. 4, pp. 183–184, Jul., Aug. 1975, Lisitsyn et al., "Measurement of the Reflection Coefficients of Mirrors".
Radiofizika, vol. 16, No. 4, pp. 531-536, Apr. 1973, Bershtein et al., "Detection and Measurement of Small Back-Scattering of Laser Radiation."

*Primary Examiner*—John K. Corbin
*Assistant Examiner*—Bruce Y. Arnold
*Attorney, Agent, or Firm*—T. W. Kennedy

[57] ABSTRACT

A measuring system for a ring laser mirror, or the like, is provided, whereby the mirror can be quickly scanned and the backscatter levels measured and presented in the form of a map which directly indicates the spots of the mirror where acceptable backscatter levels exist. When such a spot has been identified, the system of the invention is also capable of measuring the reflectivity of the spot, which normally must be approximately 99.7% to be acceptable. The system of the invention has the capability of measuring the reflectivity of the mirror in addition to measuring the backscatter in a single set-up, and without having to manipulate the mirror.

15 Claims, 6 Drawing Figures

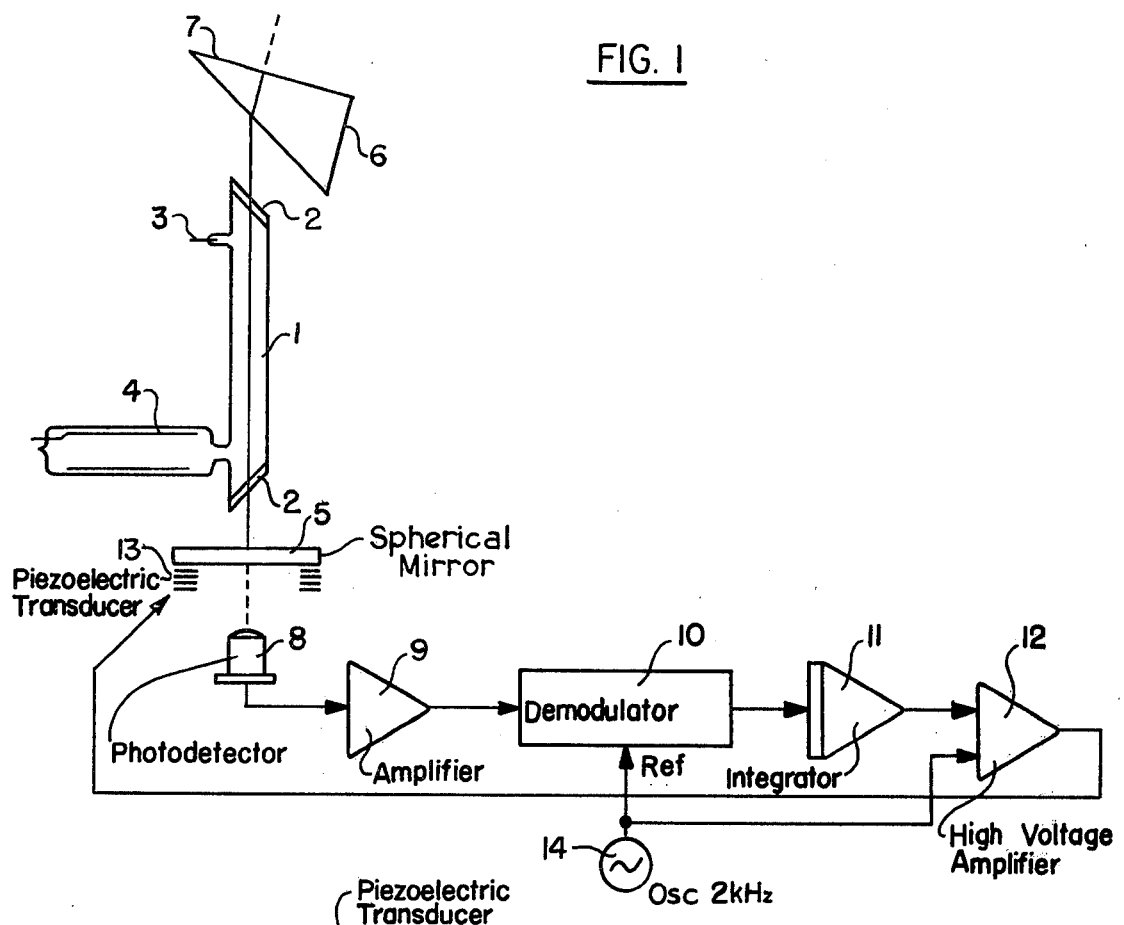
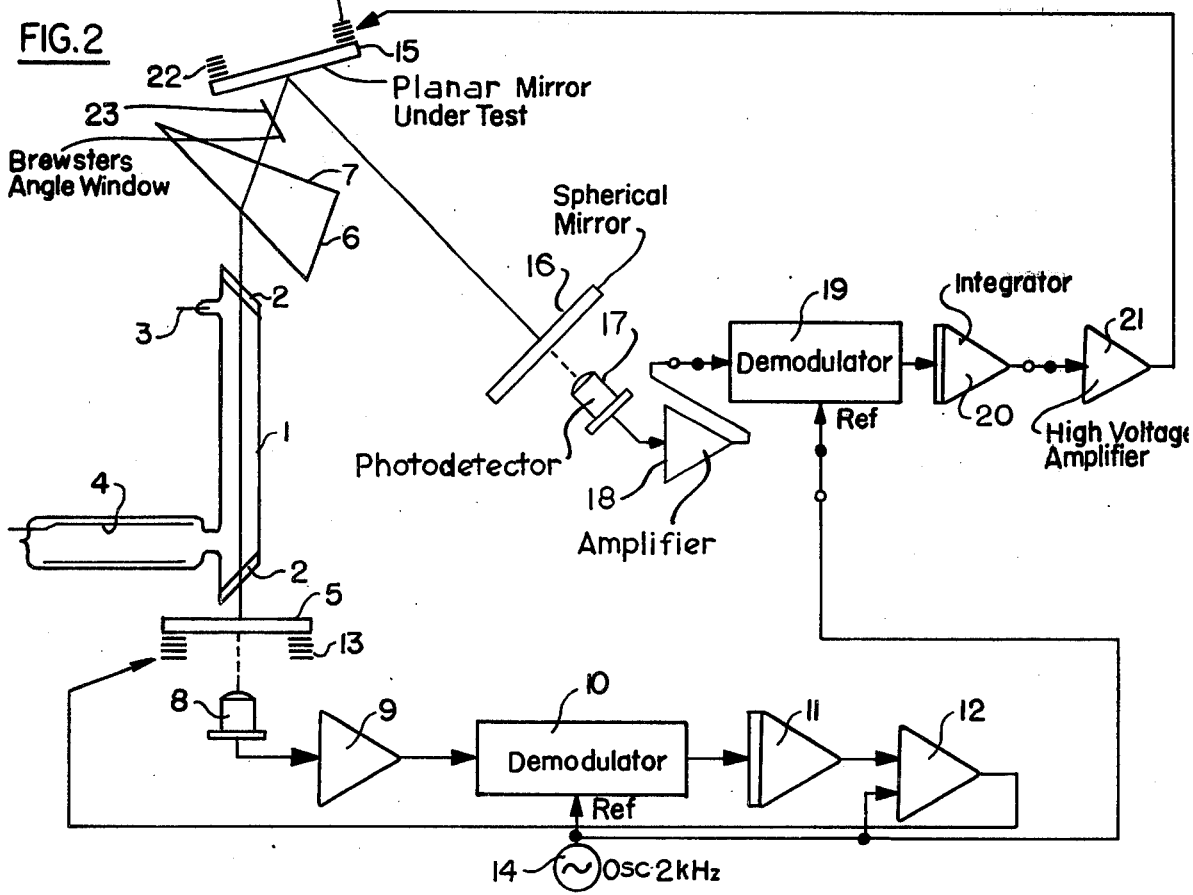

LASER MIRROR SCATTER AND REFLECTIVITY MEASURING SYSTEM

BACKGROUND OF THE INVENTION

Ring laser gyroscopes are described, for example, in U.S. Pat. Nos. 3,373,650 and 3,467,472 which issued in the name of Joseph E. Kilpatrick; and in copending application Ser. No. 782,460, filed Mar. 20, 1977, which is assigned to the present Assignee.

The ring laser gyroscopes shown and described in the patents include a triangular block which forms a triangular-shaped ring laser cavity defined by three corner mirrors. A triangular-shaped block is preferred since it requires a minimal number of mirrors. The cavity is filled by a gas which comprises, for example, helium and neon. The laser usually operates at one of two wavelengths; specifically, either at 1.15 micrometers in the infrared spectral band, or at 0.63 micrometers in the visible wavelength region.

Through proper choice of the ratios of the two neon isotopes $Ne^{20}$ and $Ne^{22}$ in the gas mixture, two monochromatic laser beams are created. The two laser beams respectively travel in clockwise and counterclockwise directions around the triangular cavity in the same closed optical path.

With no angular motion about the input axis of the ring laser gyroscope, the lengths of the two laser beams are equal, and the two optical frequencies are the same. Angular movement of the prior art ring laser gyroscope in either direction about its input axis causes an apparent increase in the cavity length for the beam travelling in the direction of such angular movement and a corresponding decrease for the beam travelling in the opposite direction. Because the closed optical path is a resonant cavity providing sustained oscillation, the wavelength of each beam must also increase or decrease accordingly. Angular movement of the ring laser gyroscope in either direction about its input axis, therefore, causes a frequency differential to occur between the two beam frequencies, and which differential is proportional to the angular rate.

In accordance with the prior art practice, the two beams are extracted from the laser at its output mirror, and they are heterodyned in a beam combiner to produce an interference pattern. The interference pattern is detected by a photodetector which senses the beam frequency of the heterodyned optical frequencies of the two beams, and this beat frequency is a measure of the angular rate.

A difficulty arises in ring laser gyroscopes at low angular rates, in that the frequency differential between the two beams is small at the low rates, and the beams tend to resonate together, or "lock-in" so that the two beams oscillate at only one frequency. It therefore is impossible to read low angular rates because the frequency differential proportional to the angular rate does not exist.

It is the usual practice, as described in the patents, and in the copending applications, to introduce mechanical vibrations to the gyroscope to eliminate lock-in. However, the effects of these mechanical vibrations must be compensated in the output of the instrument, and such compensation introduces noise into the input which increases as a function of the back scatter.

Each mirror used in a ring laser typically has about one part per million backscatter, and a reflectivity of about 99.7%. It is backscatter which causes the ring laser gyroscope to lock in at the low angular rates, and it is most desirable to reduce backscatter to a minimum since, as mentioned above, the noise produced in the output due to the compensating equipment increases as a function of the backscatter.

A method for measuring backscatter in a linear laser is described in an article by I. L. Bershtein and D. P. Stepanov in Izevstiya Vysshikh Uchebnykh Zavedenii, Radiofizika, Volume 16, No. 4, Pages 531–536, April 1973. This article describes a measuring system in which a linear laser directs a beam towards a test object, and in which a test object is vibrated at a particular frequency. The system produces an output which is synchronous with the vibration frequency of the test object. Any light back scattered into the linear laser beam produces an amplitude modulation on the output which can be detected to obtain a measurement of the back scatter.

A technique which can be used to measure the reflectivity of ring laser mirrors, and the like, is described, for example, in an article by Virgil Sanders in Applied Optics, January 1977, Volume 16, No. 1, Pages 19–20. The Sanders article describes a system in which the test object forms a part of a high-Q laser cavity. A Brewster's angle window, in which the angle of incidence can be varied, and a variable loss element, are used to measure the loss due to the test object. This is achieved by reconfiguring the cavity so as to exclude the test object. The resulting decreased losses in the laser cavity are then compensated by offsetting the Brewster's angle window to produce a loss corresponding to the loss when the test object was part of the cavity. The required adjustment of the Brewster's angle window is an indication of the reflectivity of the laser mirror.

A disadvantage in the prior art systems for measuring back scatter and laser mirror reflectivity is that the two measurements must be made individually by the different systems, and by different set-ups, which makes any correlation of the two measurements difficult and time-consuming.

Moreover, the technique described in the Sanders article for measuring mirror reflectivity is, itself, most difficult and time-consuming. This is because any slight misadjustment to the laser cavity causes the cavity gain to fall below unity which, in turn, causes the laser action to cease. When that occurs, re-alignment is especially difficult, since there are no indicators as to how to readjust the laser to restore the laser action.

An important objective of the present invention is to provide a relatively uncomplicated measuring system which is simple to operate and which is capable of producing backscatter and mirror reflectivity measurements in a single set-up and in a minimum amount of time.

BRIEF DESCRIPTION OF THE DRAWINGS

FIG. 1 is a schematic representation of a typical prior art laser which is constructed to maintain laser action within the laser cavity;

FIG. 2 is a schematic representation of the measuring system of the invention configured to obtain reflectivity measurements of the laser mirror;

DETAILED DESCRIPTION OF THE ILLUSTRATED EMBODIMENT

Figure 3:
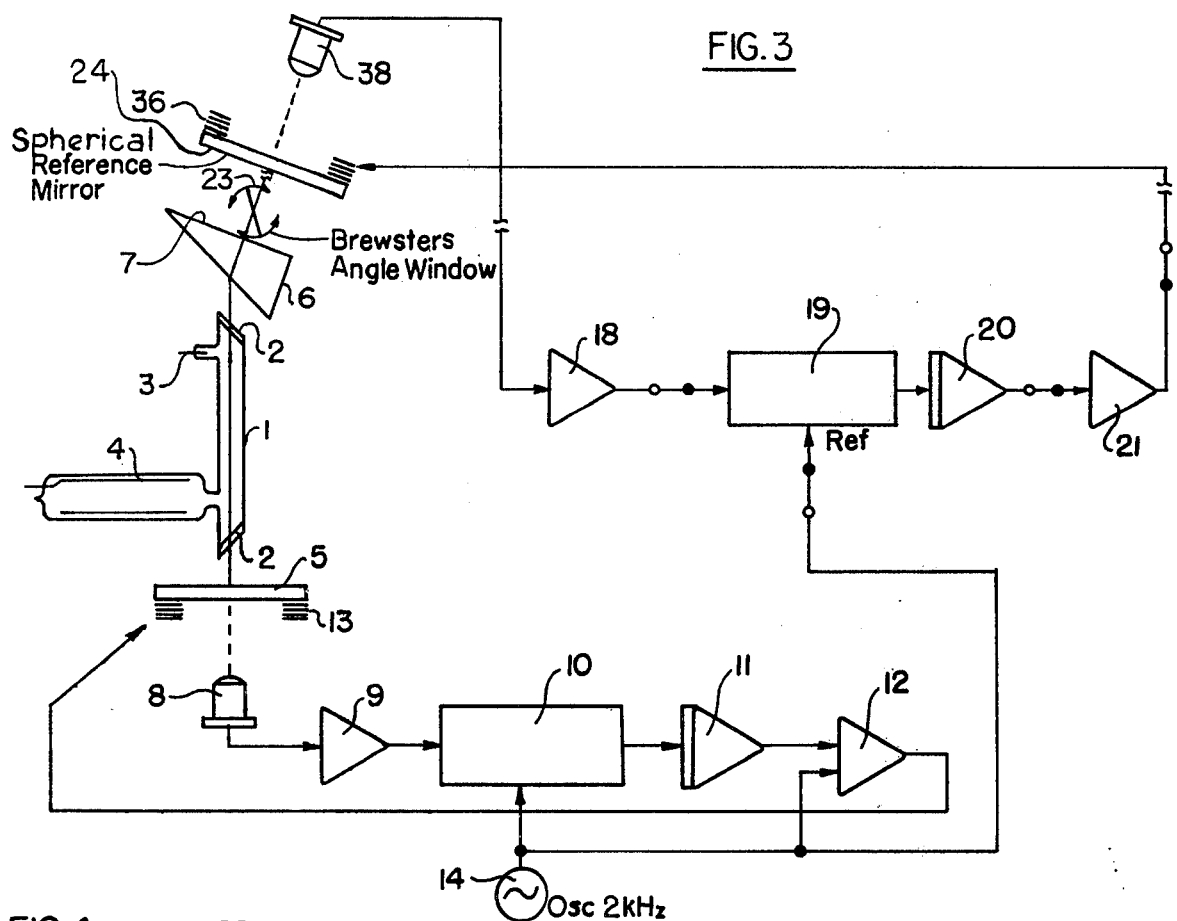
FIG. 3 is a schematic representation of the measuring system of FIG. 2 in a reference mode.

A laser system of FIG. 1 includes a plasma tube 1, with a Brewster's angle window 2 at each end. An anode 3 and a cathode 4 are mounted in the laser tube, and these electrodes are energized by an appropriate power supply (not shown) which provides an activating current to the electrodes. One side of the laser cavity of the laser system of FIG. 1 is defined by the gain tube 1, by one of the Brewster's angle windows 2, and by a spherical mirror 5. The spherical mirror 5 is provided with a highly reflective coating, in which the reflectivity, for example, is approximately 99.9%. A Littrow prism 6, with a dielectric reflective coating 7 of approximately 98%, together with the other Brewster's angle window 2, define the other side of the laser cavity.

A small amount of light leaks through mirror 5, and impinges upon a photodetector 8. The resulting electric signal from photodetector 8 is amplified in amplifier 9, and is then fed to an appropriate demodulator 10. The demodulator 10 performs its demodulating function in response to a reference signal from an oscillator 14 which may, for example, be 2kHz. The signal demodulated in demodulator 10 is integrated in an integrator 11, and is then fed to a high voltage amplifier 12. The reference signal from oscillator 14 is also introduced to the high voltage amplifier 12. The output from amplifier 12 is fed to a piezoelectric transducer 13 which is mechanically coupled to the spherical mirror 5.

The circuit described in the preceding paragraph forms a servo loop which is excited by the oscillator 14, and this servo loop serves to maintain the path length of the laser cavity centered on the gain curve. This serves to stabilize the laser, and also to provide a temporal stable output.

The laser system described above in conjunction with FIG. 1 is known to the art. Losses in the laser cavity are relatively high (approximately 2%). This results in a relatively low-Q cavity which requires high current in the plasma tube 1 to achieve a gain sufficient to activate the laser. The power output of the prior art laser of FIG. 1 can easily be made to be relatively high.

The schematic diagram of FIG. 2 includes the system of the invention which is configured as a reflectometer, and which is used to measure the reflectivity of a planar test mirror 15. The measuring system is used in conjunction with the basic laser system described in conjunction with FIG. 1.

In the system of FIG. 2, the mirror 15 being tested is positioned to reflect the laser light with a desired angle of incidence, for example, 30°. The polarization of the mirror may be chosen by appropriate geometry, and the illustrated system is used to measure, for example, p-polarization. A reference spherical mirror 16 is provided, which is identical to mirror 5; and the mirrors 5, 15 and 16 are adjusted so that all reflected light is reflected by mirror 16. The laser cavity is thus changed to a high-Q cavity.

The below-described circuit enables the high-Q cavity to be stabilized. This is achieved by measuring the leakage light through mirror 16 by a photodetector 17, and by amplifying the resulting electric signal in amplifier 18. The amplified signal is demodulated in a demodulator 19, integrated in an integrator 20, and passed through a high voltage amplifier 21 to a piezoelectric transducer 22 mechanically coupled to mirror 15. The reference signal from oscillator 14 is applied to demodulator 19.

The plasma current through tube 1 can now be reduced to a relatively low value while still maintaining laser action within the tube. The current through the tube is reduced to the point at which the laser action stops, and the threshold is noted. During these operations, a Brewster's angle window 23 between the prism 6 and the mirror 15 is adjusted to its proper Brewster's angle, at which losses in the window approach zero. The Brewster's angle window is approximately 0.004 inches thick, and is formed, for example, of fused silica.

In order that the reflectivity of the test mirror 15 may be computed, a reference measurement is necessary, which is achieved by the system shown in FIG. 3. The reference reading is obtained by removing the test mirror 15, and substituting a reference mirror 24.

The leakage light through the reference mirror 24 is measured by a photodetector 38, whose output is fed to amplifier 18, which, in conjunction with the components 19, 20 and 21, completes the servo loop to a piezoelectric transducer 36 associated with the reference mirror 24.

The laser cavity now has its lowest loss, and its highest Q, and the cavity will now operate at the plasma current corresponding to the previous lasing threshold. The Brewster's angle window 23 then is rotated away from its previous position so that the lasing threshold is again approached. The losses added to the laser cavity by rotating the Brewster's angle window 23 corresponds exactly to the losses in the mirror 15 under test.

When the angle is known through which the Brewster's angle window 23 has been rotated, the actual reflectivity losses of the mirror 15 under test can be calculated using Snell's law of reflection. By utilizing a relatively thin, 0.004 inch, Brewster's angle window, no re-alignment of the laser cavity is necessary when making the measurements described above.

Figure 4:
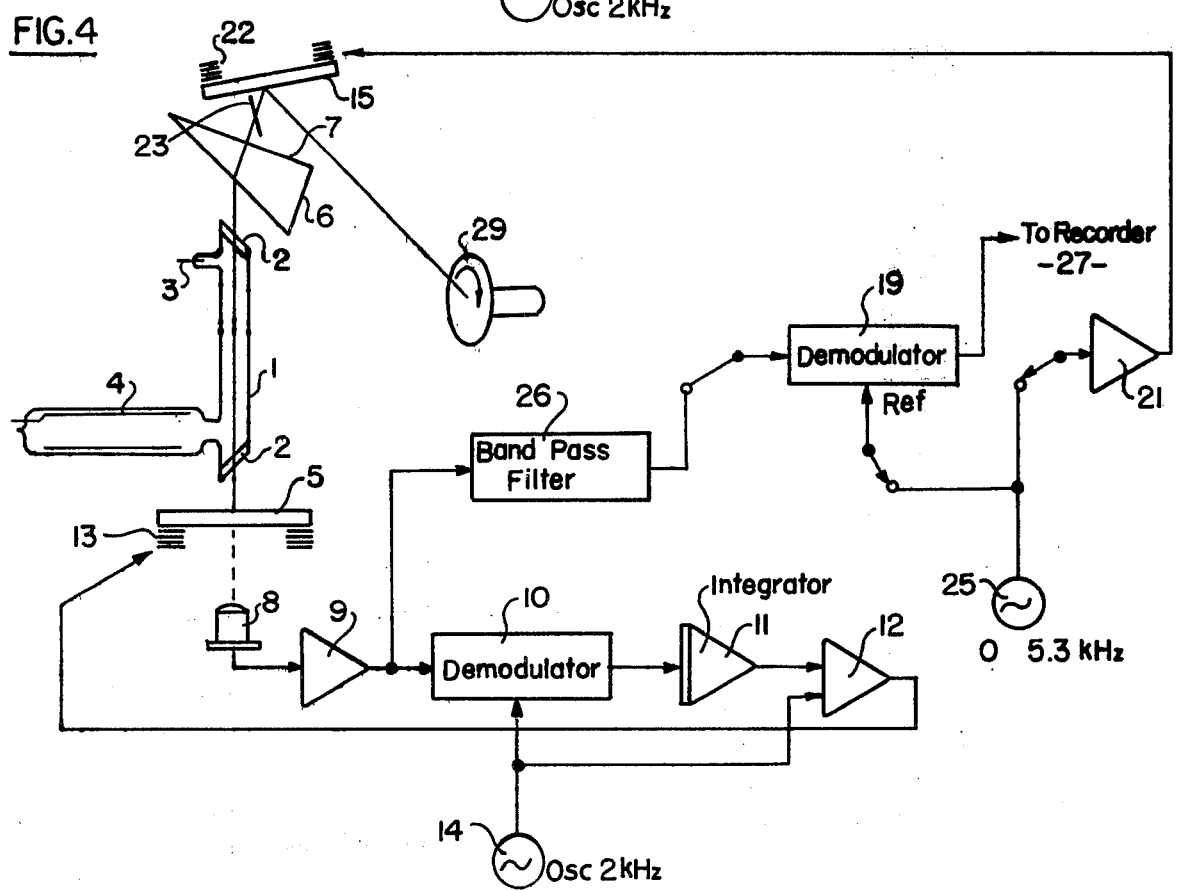
FIG. 4 is a schematic representation of the measuring system of the invention configured to measure backscatter of the laser mirror.

The measuring system of the invention configured as a scatterometer for measuring the back scatter of the mirror 15 under test is shown in FIG. 4.

In the system of FIG. 4, a band-pass filter 26 is connected to the output of amplifier 9, and the output of the band-pass filter is introduced to demodulator 19. The output of the demodulator is applied to a recorder 27. A second oscilator 25 is provided which generates a reference signal of a frequency of, for example, 5.3 kHz, and this reference signal is applied to demodulator 19, and through the high voltage amplifier 21 to the piezoelectric transducer 22 mechanically coupled to the mirror 15 under test.

The circuit described above produces vibrations in the test mirror 15, and the light backscattered into the laser causes the output of the laser to fluctuate in synchronism with vibrations of the test mirror 15. The fluctuations are detected by the photodetector 8, and the resulting electric signal is passed through band-pass filter 26 to demodulator 19. The demodulated output of the demodulator is fed to the recording device 27, where the amount of back scattered light can be directly indicated.

The test mirror 15 may be mechanically scanned along two coordinate axes to facilitate mapping of the back scatter characteristics of the test mirror. By suitably processing the information, that is, by processing the position coordinates for the test mirror and the scatter output, an isometric map may be produced, where scatter centers are represented as mountains. The test mirror 15 may be scanned by means of any suitable scanning mechanism, not shown.

It should be noted that for proper operation of the system, the two oscillators 14 and 25 must operate at different frequencies. In order that the reflected beam will not scatter back into the laser tube 1, the reflected beam is directed to a black rotating wheel 29. The portion of the laser beam which leaks through the test mirror 15 may be measured by an appropriate photodetector, whose output may be compared with the output of photodetector 8 to calculate the transmission of the test mirror 15.

Figures 5, 6:
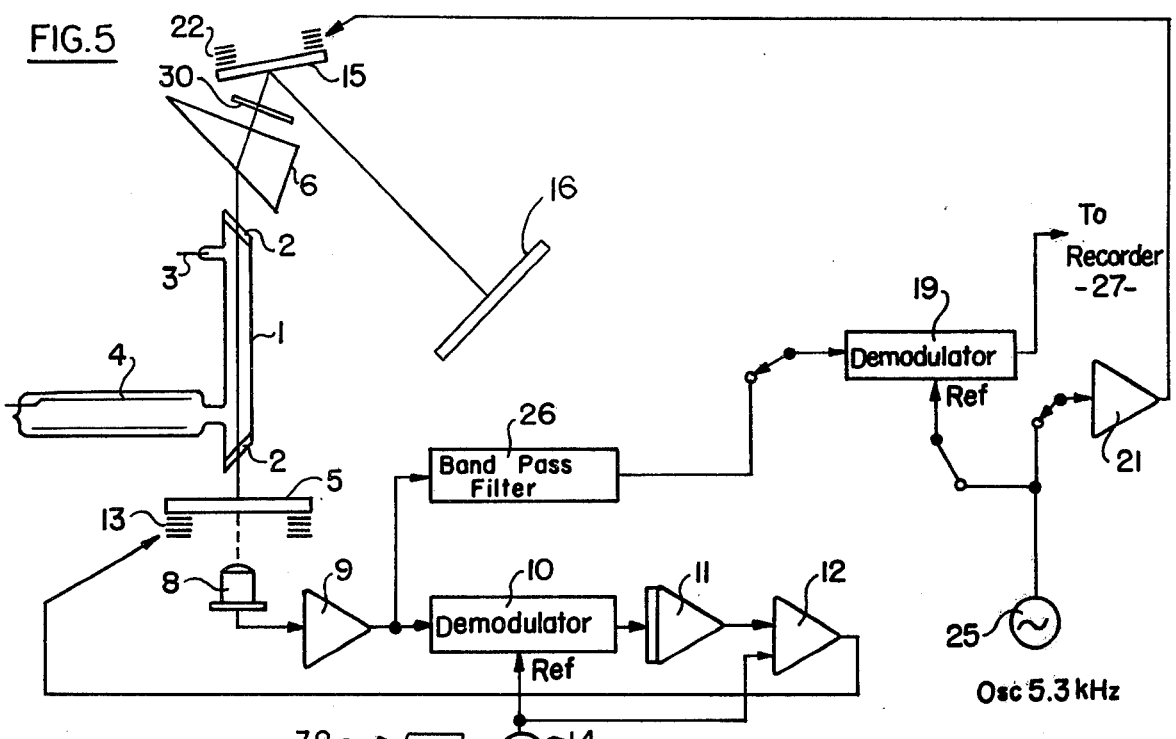
FIG. 5 is a schematic representation of the system of FIG. 4 in a calibrating mode.
FIG. 6 is a schematic representation of the combined measuring system of the invention which is capable of measuring backscatter and reflectivity of a laser mirror without any need for two separate set-ups, or to manipulate the mirror between the two measurements.

In order to calibrate the scatterometer of FIG. 4, the calibration system of FIG. 5 is used. In the calibration system, all the available light reflected from the test mirror 15 is directed to mirror 16, which reflects the light back to the test mirror 15. The system can now be calibrated by inserting an attenuator 30 between the Littrow prism 6 and the test mirror 15. By the selection of an appropriate attenuator, the output recorded on recorder 27 can be brought to indicate on the same scale as with the previous measurement of the scattered light in the system of FIG. 4. The actual scatter measurement can thus easily be calibrated.

The system of FIG. 6 is a composite measuring system which, in accordance with the invention operates as a reflectometer in one mode, and as a scatterometer in a second mode. The system of FIG. 6 incorporates the systems of FIGS. 2 and 4, and includes switches S1, S2, S3, S4 and S5 to connect the composite system as the reflectometer of FIG. 2 in one switching mode, and to connect the system as the scatterometer of FIG. 4 in a second switching mode.

Two mirrors 16 and 24 may be used for calibrating the system in the scatter mode, the mirror 24 being mechanically coupled to a piezoelectric transducer 36 which is activated by the output of high voltage amplifier 21. These two mirrors can be easily calibrated, and with their relative reflectivity known, no tedious readjustments are necessary when the system of FIG. 6 is set to its reflectometer mode.

The present invention provides, therefore, an improved system which is capable of measuring both scatter and reflectivity in a single set-up, and by means of a simple switching operation, so as to provide a direct correlation between scatter and reflectivity of a test mirror. The system of the invention is easier to operate when in its reflectometer mode than the prior art systems, because there is no tendency for the laser to cease lasing, even if the test mirror is misaligned. Moreover, due to the relatively small thickness of the Brewster's angle window, no realignment of the laser cavity is necessary when the window is rotated.

The invention provides, thereof, an improved dual stabilized system in which a laser cavity is stabilized by dual servo systems, in which scatter and reflectivity measurements may be made in a single set-up, and which provides a direct correlation between scatter and reflectivity. As mentioned above, the system of the invention is advantageous in that the basic laser light source never needs adjustment. Also, the use of a relatively thin Brewster's angle window, permits rotation of the window without the concomitant need to re-align the laser cavity.

While particular embodiments of the invention have been shown and described, modifications may be made. It is intended in the claims to cover all modifications which come within the true spirit and scope of the invention.

What is claimed is:

1. A system for testing the reflective characteristics of an optical element, said system including:
   a laser light source including first mirror means defining one side of the cavity of the laser source, and optical means defining a second side of the cavity of the laser source;
   means for supporting the optical element to be tested in the path of a beam of laser light issuing from the second side of the laser source;
   a Brewster's angle window interposed between the optical means and the optical element to be tested, said Brewster's angle window being adjustable to an angle at which losses therein approach zero;
   a first servo circuit including a first photodetector means positioned to the rear of said first mirror means and responsive to light leaking therethrough, and first electromechanical transducer means mechanically coupled to the first mirror means for stabilizing the laser source;
   a second mirror means positioned to receive light from the optical element to be tested and to reflect the light back through the optical element and through the optical means to the laser source; and
   a second servo circuit including a second photodetector means positioned to the rear of said second mirror means and responsive to light leaking therethrough, and second electromechanical transducer means mechanically coupled to the optical element supporting means for further stabilizing the laser light source.

2. The system defined in claim 1, in which the Brewster's angle window has a thickness of the order of 0.004 inches.

3. The system defined in claim 1, in which said optical means which defines the second side of the cavity of the laser source comprises a Littrow prism with a dielectric reflective coating thereon.

4. The system defined in claim 1, and which includes a first reference mirror means positioned to receive the laser light from the second side of the laser source when the optical element under test is removed, third photodetector means positioned to the rear of said first reference mirror means for receiving light leaking through said first reference mirror means and for generating an electrical signal corresponding thereto; third electromechanical transducer means mechanically coupled to the reference mirror means; and means for connecting the output of the third photodetector means to the second servo circuit and for connecting the output of the second servo circuit to the third electromechanical transducer means.

5. The system defined in claim 1, and which includes electromechanical transducer means mechanically coupled to the optical element supporting means; oscillator means; and means connecting said oscillator means to said electromechanical transducer means to cause the optical element under test to vibrate and introduce backscattered light into the laser light source.

6. The system defined in claim 1, and which includes second electromechanical transducer means mechanically coupled to the optical element supporting means; oscillator means; means for connecting said oscillator means to said second electromechanical transducer means to cause the optical element under test to vibrate and introduce back scattered light into the laser source causing the electric signal generated by said first photodetector means to be modulated by a signal synchronized with the vibrations of the element under test; filter means; and means for connecting said filter means to the output of said first photodetector means for causing the filter means to select the modulating signal so as to produce a reading of the amount of light backscattered from the optical element under test into the laser source.

7. The system defined in claim 6, in which the optical element under test is mechanically scanned in two coordinate directions.

8. The system defined in claim 6, and which includes second mirror means positioned to receive light from the optical element to be tested and to reflect the light back through the optical element to the laser source; and adjustable light attenuating means positioned between the optical element to be tested and the second side of the laser source for calibrating the aforesaid reading.

9. A system for testing the reflective characteristics of an optical element, including:
- a laser light source including first mirror means defining one side of the cavity of the laser source, and optical means defining a second side of the cavity of the optical source;
- means for supporting the optical element to be tested in the path of a beam of laser light from the second side of the laser source;
- electromechanical transducer means coupled to the optical element supporting means;
- oscillator means;
- means connecting said oscillator means to said electromechanical transducer means to cause the optical element under test to vibrate and to direct backscattered light into the laser source;
- a first servo system including a first photodetector means positioned to the rear of said first mirror means and responsive to light leaking therethrough, and second electromechanical transducer means mechanically coupled to the first mirror means for stabilizing the laser light source;
- means to modulate the electric signal generated by said first photodetector means with a signal synchronized with the vibrations of the element under test;
- filter means;
- means for connecting the filter means to the output of the first photodetector means for causing the filter means to select the modulating signal so as to produce a reading of the amount of backscattered light from the optical element under test; and
- means to mechanically scan the optical element under test in two coordinate directions.

10. The system defined in claim 9, and which includes a black rotating wheel for absorbing the laser beam reflected from the optical element being tested.

11. The system defined in claim 9, and which includes mirror means positioned to receive light from the optical element being tested and to reflect the light back through the optical element to the laser source, and a second adjustable light attenuating means positioned between the optical element being tested and the second side of the laser source for calibrating the aforesaid reading.

12. A system for testing the reflective characteristics of an optical element, said system including:
- a laser light source including first mirror means defining one side of the cavity of the laser source, and optical means defining a second side of the cavity of the laser source;
- means for supporting the optical element to be tested in the path of a beam of laser light issuing from the second side of the laser source;
- a Brewster's angle window interposed between the optical means and the optical element to be tested, said Brewster's angle window being adjustable to an angle at which losses therein approach zero;
- electromechanical transducer means mechanically coupled to the optical element supporting means; oscillator means; and means connecting said oscillator means to said electromechanical transducer means to cause the optical element under test to vibrate and introduce backscattered light into the laser light source;
- means to scan the optical element under test mechanically in two coordinate directions.

13. A system for testing the reflective characteristics of an optical element, said system including:
- a laser light source including first mirror means defining one side of the cavity of the laser source, and optical means defining a second side of the cavity of the laser source;
- means for supporting the optical element to be tested in the path of a beam of laser light issuing from the second side of the laser source;
- a Brewster's angle window interposed between the optical means and the optical element to be tested, said Brewster's angle window being adjustable to an angle at which losses therein approach zero;
- a first servo circuit including, a first photodetector means positioned to the rear of said first mirror means and responsive to light leaking therethrough, and first electromechanical transducer means mechanically coupled to the first mirror means, for stabilizing the laser source;
- second electromechanical transducer means mechanically coupled to the optical element supporting means; oscillator means, means for connecting said oscillator means to said second electromechanical transducer means to cause the optical element under test to vibrate and introduce backscattered light into the laser source causing the electric signal generated by said first photodetector means to be modulated by a signal synchronized with the vibrations of the element under test; filter means; and means for connecting said filter means to the output of said first photodetector means for causing the filter means to select the modulating signal so as to produce a reading of the amount of light backscattered from the optical element under test into the laser source; and
- second mirror means positioned to receive light from the optical element to be tested and to reflect the light back through the optical element to the laser source; and adjustable light attenuating means positioned between the optical element to be tested and the second side of the laser source for calibrating the aforesaid reading.

14. A system for testing the reflective characteristics of an optical element, including:
- a laser light source including first mirror means defining one side of the cavity of the laser source, and optical means defining a second side of the cavity of the optical source;
- means for supporting the optical element to be tested in the path of a beam of laser light from the second side of the laser source;
- electromechanical transducer means coupled to the optical element supporting means;
- oscillator means;
- means connecting said oscillator means to said electromechanical transducer means to cause the optical element under test to vibrate and to direct backscattered light into the laser source; and
- a black rotating wheel for absorbing the laser beam reflected from the optical element being tested.

15. A system for testing the reflective characteristics of an optical element, including:
- a laser light source including first mirror means defining one side of the cavity of the laser source, and optical means defining a second side of the cavity of the optical source;
- means for supporting the optical element to be tested in the path of a beam of laser light from the second side of the laser source;
- electromechanical transducer means coupled to the optical element supporting means;
- oscillator means;
- means connecting said oscillator means to said electromechanical transducer means to cause the optical element under test to vibrate and to direct backscattered light into the laser source;
- mirror means positioned to receive light from the optical element being tested and to reflect the light back through the optical element to the laser source; and
- a second adjustable light attenuating means positioned between the optical element being tested and the second side of the laser source for calibrating the aforesaid reading.

* * * * *